(12) United States Patent
Wang et al.

(10) Patent No.: US 10,662,190 B2
(45) Date of Patent: *May 26, 2020

(54) PROCESS FOR PREPARING 5R-[(BENZYLOXY) AMINO] PIPERIDINE-2S-CARBOXYLATE AND OXALATES THEREOF

(71) Applicant: XINFA PHARMACEUTICAL CO., LTD, Dongying (CN)

(72) Inventors: Baolin Wang, Dongying (CN); Yuxin Qi, Dongying (CN); Yinlong Zhao, Dongying (CN); Yuqi Teng, Dongying (CN); Jun Chen, Dongying (CN); Lizhu Ju, Dongying (CN); Xinfa Li, Dongying (CN)

(73) Assignee: XINFA PHARMACEUTICAL CO., LTD, Dongying (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/345,744

(22) PCT Filed: Mar. 2, 2018

(86) PCT No.: PCT/CN2018/077915
§ 371 (c)(1),
(2) Date: Apr. 29, 2019

(87) PCT Pub. No.: WO2019/033746
PCT Pub. Date: Feb. 21, 2019

(65) Prior Publication Data
US 2019/0256514 A1    Aug. 22, 2019

(30) Foreign Application Priority Data
Aug. 18, 2017 (CN) .......................... 2017 1 0714244

(51) Int. Cl.
*C07D 471/08* (2006.01)
*C07D 211/60* (2006.01)
*C07C 51/41* (2006.01)
*C07C 55/07* (2006.01)

(52) U.S. Cl.
CPC ............ *C07D 471/08* (2013.01); *C07C 51/41* (2013.01); *C07C 55/07* (2013.01); *C07D 211/60* (2013.01)

(58) Field of Classification Search
CPC .............................. C07D 471/08; C07C 51/41
USPC ....................................................... 546/121
See application file for complete search history.

(56) References Cited

PUBLICATIONS

CN-107540601-A Li XINFA (Year: 2016) text.*
CN-107540601-ALINFA figure 1. (Year: 2016).*

* cited by examiner

*Primary Examiner* — Rita J Desai
(74) *Attorney, Agent, or Firm* — CBM Patent Consulting, LLC

(57) ABSTRACT

It relates to improved processes of preparing 5R-[(benzyloxy) amino] piperidine-2S-carboxylate and oxalate thereof. In the present invention, L-glutamic acid or L-glutamic acid sodium salt as the starting material is reacted with chloroactic acid under an alkaline condition via a substitution reaction to obtain compound III; then, compound III is reacted with alcohol in the presence of acid reagent via esterification reaction to obtain compound IV; under the action of strong base, compound IV is subjected to intramolecular condensation into ring, hydrolysis-decarboxylation, and esterification to obtain compound V; compound V is condensed with benzyloxy amine hydrochloride salt in the presence of alkaline to obtain compound VI; compound VI is subjected to reduction and chiral resolution to obtain 5R-[(benzyloxy) amino] piperidine-2S-carboxylate oxalate (IIb) which is then neutralized to obtain 5R-[(benzyloxy) amino] piperidine-2S-carboxylate (IIa).

10 Claims, 3 Drawing Sheets

PROCESS FOR PREPARING 5R-[(BENZYLOXY) AMINO] PIPERIDINE-2S-CARBOXYLATE AND OXALATES THEREOF

FIELD

The present invention relates to the field of pharmaceutical biochemical engineering, and more particularly relates to a process for preparing 5R-[(benzyloxy) amino] piperidine-2S-carboxylate, and oxalates thereof.

BACKGROUND

5R-[(benzyloxy)amino] piperidine-2S-carboxylate and 5R-[(benzyloxy)amino] piperidine-2S-carboxylate oxalate are key intermediates for preparing avibactam.

As a non-β-lactam inhibitor, one of diazabicyclooctanone compounds, avibactam may inhibit type-A (including ESBL and KPC) and type C β-lactamases. When administered in combination with various types of cephalosporins and carbapenem antibiotics, avibactam has a broad spectrum activity against bacteria, particularly has a significant activity against the *Escherichia coli* and *Klebsiella pneumoniae* containing ultra-broad spectrum β-lactamases, *Escherichia coli* containing excessive AmpC enzyme, and *Escherichia coli* containing both AmpC and ultra-broad spectrum β-lactamases. The sodium salt form of avibactam is shown in Formula I, whose CAS number is 1192491-61-4, with a chemical name of [(1R,2S,5R)-2-(aminocarbonyl)-7-oxo-1,6-diazabicyclo[3.2.1]oct-6-yl] sodium sulphate.

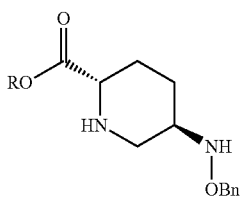

IIa

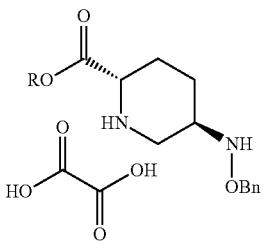

(IIb)

Forms of Oxalate

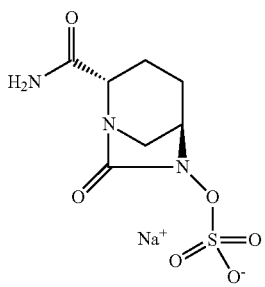

I

5R-[(benzyloxy)amino]piperidine-2S-carboxylate is a key intermediate for preparing avibactam (I). The patent WO2012172368 discloses a synthesis process for 5R-[(benzyloxy)amino]piperidine-2S-carboxylate and avibactam; the U.S. patents US2010197928 and US2013012712 disclose a synthesis of 5R-[(benzyloxy)amino]piperidine-2S-carboxylate (see scheme 1). Briefly, the N-protected L-pyroglutamate as the starting material is ring-opened with trimethylsulfoxonium iodide to add the carbon chain, the carbonyl of it is converted to imine by benzyloxyimino, and then the intermediate is deprotected under an acidic condition to remove protecting group, cyclized under an alkaline condition, and finally reduced by a reducing agent and subjected to chiral resolution to obtain a product IIb. The starting material and trimethylsulfoxonium iodide used in this process are expensive, and the total yield is not high.

Scheme 1

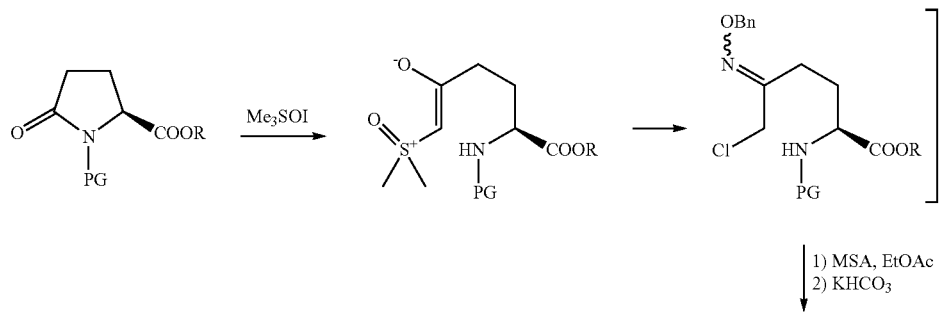

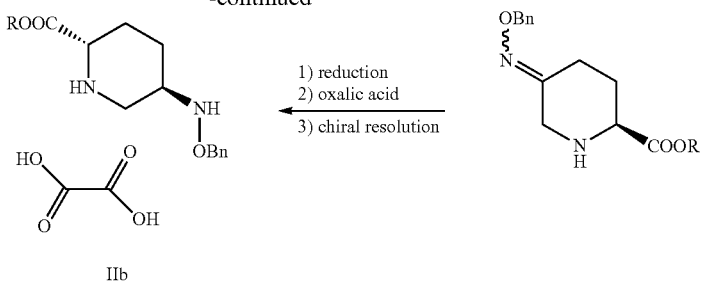

IIb

US20140275001 discloses another synthesis process (scheme 2), wherein the N-protected L-pyroglutamate is still utilized as the starting material and is ring-opened with trimethylsulfoxonium iodide to add the carbon chain. The difference lies in that in the patent US20140275001, the cyclization is firstly carried out by an iridium catalyst to obtain an alcohol with S-conformation through selective reduction; and then inversion of configuration is realized by using N-benzyloxy-2-nitrobenzenesulfonamide and hydroxyl is converted into amino; 2-nitrobenzenesulfonyl chloride group is first removed under the action of lithium hydroxide and mercaptoacetic acid, and then the N-protecting group is removed by trifluoroacetic acid to obtain the product. The process has a complicated operation and uses the expensive iridium catalyst, and the total yield is only 15%.

protection and deprotection, such that the operations are very complicated; besides, they use a large amount of solvents and discharge a large amount of waste water, waste gas, and waste residuals, which are not environment-friendly and have a low atomic economy. Meanwhile, the two methods have a low yield and do not facilitate industrial production.

SUMMARY

To solve the drawbacks in the prior arts, the present invention provides an improved process for preparing intermediates for avibactam, and said intermediates are 5R-[(benzyloxy)amino]piperidine-2S-carboxylate (IIa) and 5R-[(benzyloxy)amino]piperidine-2S-carboxylate oxalate (IIb);

Scheme 2

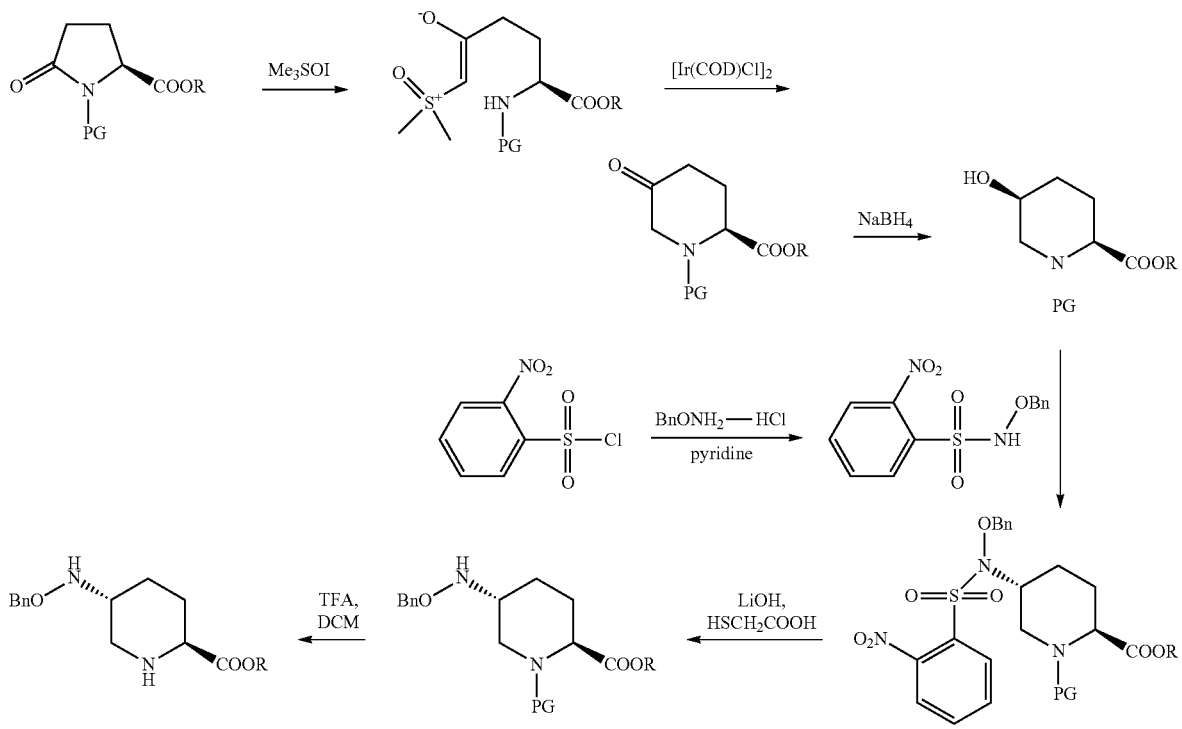

Scheme 1 and Scheme 2 above adopt relatively expensive starting materials and a method of adding the carbon chain by trimethylsulfoxonium iodide; further, Scheme 2 uses the expensive iridium catalyst. The two reaction processes need in other words, the present invention provides an improved process for preparing 5R-[(benzyloxy)amino]piperidine-2S-carboxylate (IIa) and 5R-[(benzyloxy)amino]piperidine-2S-carboxylate oxalate (IIb).

The present invention uses L-glutamic acid or L-glutamic acid sodium salt as the starting material, which is inexpensive and easily accessible. The reactions in respective steps have a high selectivity and a high yield of target products.

Definitions of Terms:

Compound III: N-carboxymethyl-L-glutamic acid (III);

Compound IV: N-alkoxycarbonyl methyl-L-glutamic acid diester (IV);

Compound V: piperidine-5-one-2S-carboxylate (V);

Compound VI: 5-[(benzyloxy)imino]piperidine-2S-carboxylate (VI);

Target Product 1: 5R-[(benzyloxy)amino]piperidine-2S-carboxylate oxalate (IIb);

Target Product 2: 5R-[(benzyloxy)amino]piperidine-2S-carboxylate (IIa);

The numbering of the compounds in the specification is completely consistent with the numbering of their structural formulae, and they have the same references.

The technical solution of the present invention is provided below:

A process for preparing 5R-[(benzyloxy) amino] piperidine-2S-carboxylate oxalate, comprising:

(1) subjecting L-glutamic acid or L-glutamic acid sodium salt to a substitution reaction with chloroactic acid at 10° C. to 70° C. under an alkaline condition provided by an inorganic base or an organic base to obtain N-carboxymethyl-L-glutamic acid (III);

(2) subjecting N-carboxymethyl-L-glutamic acid (III) and alcohol to an esterification reaction in the presence of an acid reagent to prepare N-alkoxycarbonyl methyl-L-glutamic acid diester (IV); wherein the acid reagent is thionyl chloride or triphosgene;

(3) subjecting N-alkoxycarbonyl methyl-L-glutamic acid diester (IV) to an intramolecular condensation reaction under the action of a solvent and a strong base; and subjecting the condensed product to a hydrolysis-decarboxylation reaction and an esterification reaction to obtain piperidine-5-one-2S-carboxylate (V);

wherein the solvent is tetrahydrofuran, 2-methyltetrahydrofuran or methoxycyclopentane;

the hydrolysis-decarboxylation reaction is carried out under the action of an inorganic acid;

the esterification reaction is carried out in the presence of thionyl chloride or triphosgene and alcohol;

(4) condensing the obtained piperidine-5-one-2S-carboxylate (V) and benzyloxyamine hydrochloride in a solvent in the presence of the organic base to obtain 5-[(benzyloxy) imino] piperidine-2S-carboxylate (VI);

(5) subjecting 5-[(benzyloxy)imino] piperidine-2S-carboxylate (VI) to a selective reduction and a chiral resolution to obtain 5R-[(benzyloxy) amino] piperidine-2S-carboxylate oxalate (IIb).

A process for preparing 5R-[(benzyloxy) amino] piperidine-2S-carboxylate (IIa) according to the present invention comprises the above steps of preparing 5R-[(benzyloxy) amino] piperidine-2S-carboxylate oxalate (IIb), and a step of neutralizing the obtained 5R-[(benzyloxy) amino] piperidine-2S-carboxylate oxalate (IIb) to obtain 5R-[(benzyloxy) amino] piperidine-2S-carboxylate (IIa).

The scheme (Scheme 3) of the present invention is provided below:

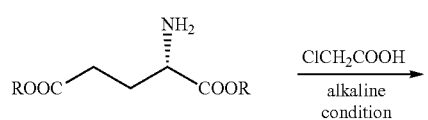

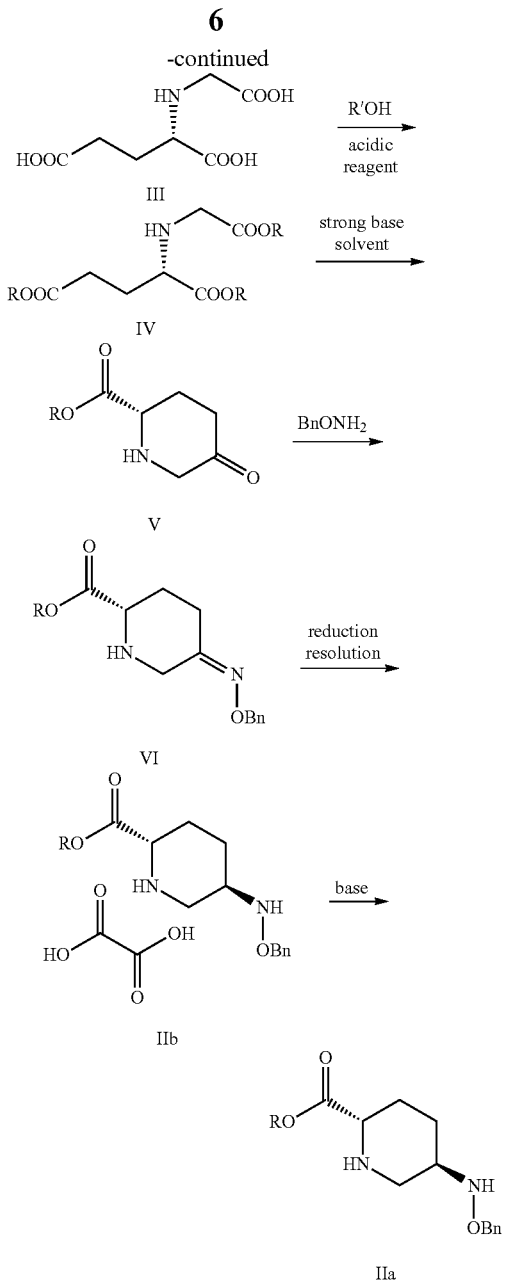

In the scheme, R denotes H, alkali metal ion or alkaline earth metal ion; R' is a $C_{1-6}$ aliphatic group, such as methyl, ethyl, n-propyl, isopropyl, n-butyl, isobutyl, tert-butyl, n-pentyl, isopentyl, tert-pentyl, hexyl with a general formula $C_6H_{13}$—; or optionally substituted $C_{6-9}$ aryl alcohol or aryl alcohol substituted with alkyl, e.g., benzyl, o-methylbenzyl or p-methylbenzyl.

According to the present invention, further, the alkaline condition in step (1) is provided by adding an inorganic base or an organic base, wherein the inorganic base is selected from the group consisting of sodium hydroxide, potassium hydroxide, potassium carbonate, sodium carbonate, calcium carbonate, potassium hydrogencarbonate, sodium hydrogencarbonate, calcium hydrogencarbonate, potassium acetate, sodium acetate or calcium acetate and a combination thereof; and the organic base is selected from the group consisting of trimethylamine, triethylamine, or tri-n-butylamine, and a combination thereof.

According to the present invention, preferably, in step (1), L-glutamic acid sodium salt is one of L-glutamic acid monosodium salt and L-glutamic acid disodium salt.

According to the present invention, further, in step (1), a mole ratio between chloroactic acid:the inorganic base or organic base: L-glutamic acid or L-glutamic acid sodium salt is (1.0-3.0):(1.0-4.0):1.

According to the present invention, preferably, the reaction temperature in step (1) ranges from 25° C. to 55° C. and the reaction duration ranges from 1 hour to 9 hours. Further, the reaction temperature ranges from 30° C. to 45° C. and the reaction duration ranges from 3 hours to 7 hours.

According to the present invention, in step (2), when the acid reagent is thionyl chloride, a molar ratio between thionyl chloride and N-carboxymethyl-L-glutamic acid (III) is (3.0-6.0):1; and the temperature for the esterification reaction ranges from 30° C. to 95° C., preferably from 60° C. to 85° C.

According to the present invention, in step (2), when the acid reagent is triphosgene, a mole ratio between triphosgene and N-carboxymethyl-L-glutamic acid (III) is (1.0-2.0):1; and the temperature for the esterification reaction ranges from 50° C. to 100° C., preferably from 70° C. to 90° C.

According to the present invention, in step (2), a duration for the esterification reaction ranges from 1 hour to 8 hours; preferably from 5 hours to 7 hours.

According to the present invention, in step (2), the alcohol is any $C_{1-6}$ saturated fatty alcohol, preferably selected from the group consisting of methanol, ethanol, n-propanol, isopropanol, n-butanol, isobutanol, tert-butanol, n-pentanol, isopentanol, tert-pentanol, and hexanol; or the alcohol is optionally substituted $C_{6-9}$ aryl alcohol or aryl alcohol substituted with alkyl, preferably selected from one of benzyl alcohol, o-methyl benzyl alcohol, and p-methyl benzyl alcohol.

According to the present invention, preferably, a mass ratio between the alcohol and N-carboxymethyl-L-glutamic acid (III) is (1-30):1, further preferably (10-25):1. Further preferably, the mass ratio between the alcohol and N-carboxymethyl-L-glutamic acid (III) is (5.0-15.0):1.

According to the present invention, in step (3), a mass ratio between the solvent and N-alkoxycarbonyl methyl-L-glutamic acid diester (IV) ranges from 4:1 to 20:1. The strong base is selected from the group consisting of sodium hydride, sodium methoxide, sodium ethoxide, sodium t-butoxide, potassium t-butoxide and sodium benzyloxide; a molar ratio between the strong base and N-alkoxycarbonyl methyl-L-glutamic acid diester (IV) is (1.0-2.0):1.

According to the present invention, a reaction temperature for intramolecular condensation and cyclization in step (3) ranges from −20° C. to 30° C.; in order to ensure a safe charging and prevent over-temperature, particularly preferably, the temperature is controlled not to exceed 0° C. when N-alkoxycarbonyl methyl-L-glutamic acid diester (IV) is added dropwise; after completion of the addition, the reaction temperature ranges from 20° C. to 25° C. The reaction duration for the intramolecular condensation and cyclization ranges from about 2 hours to 5 hours.

According to the present invention, in step (3), the temperature for the hydrolysis and decarboxylation reaction ranges from 20° C. to 60° C., preferably from 20° C. to 30° C.; and the duration for the hydrolysis-decarboxylation reaction ranges from 2 hours to 6 hours.

According to the present invention, in step (3), the alcohol used in the esterification reaction is methanol, ethanol or benzyl alcohol, and a mass ratio between the alcohol and N-alkoxycarbonyl methyl-L-glutamic acid diester (IV) is (1-30):1; further preferably (5-15): 1. The molar ratio between thionyl chloride or triphosgene and N-alkoxycarbonyl methyl-L-glutamic acid diester (IV) is (0.3-3.0): 1, and the temperature for the esterification reaction ranges from 50° C. to 100° C.; preferably, the duration for the esterification reaction ranges from 1 hour to 8 hours.

According to the present invention, in step (4), the solvent is selected from the group consisting of ethyl acetate, dichloromethane, chloroform, 1,2-dichloroethane, benzene, and methylbenzene and a combination thereof; the organic base is selected from the group consisting of trimethylamine, triethylamine, and tri-n-butylamine and a combination thereof. A mass ratio between the solvent and piperidine-5-one-2S-carboxylate (V) ranges from 4:1 to 12:1.

In step (4), a molar ratio between benzyloxyamine hydrochloride and piperidine-5-one-2S-carboxylate (V) is (0.9-1.5):1; and the temperature for the condensation reaction ranges from 40° C. to 80° C., preferably from 50° C. to 65° C. In step (4), a duration for the condensation reaction ranges from 2 hours to 5 hours.

According to the present invention, preferably, in step (5), the selective reduction is carried out by adding a reducing agent in ethyl acetate in the presence of concentrated sulfuric acid; a mass ratio between ethyl acetate and 5-[(benzyloxy)imino] piperidine-2S-carboxylate (VI) ranges from 5:1 to 20:1; further preferably, the reducing agent is selected from the group consisting of sodium borohydride, sodium tricyanoborohydride, sodium triacetoxyborohydride, sodium tripropionyloxyborohydride, potassium borohydride, potassium tricyanoborohydride, potassium triacetoxyborohydride or potassium triproloxyborohydride. Preferably, a molar ratio between the reducing agent and 5-[(benzyloxy)imino] piperidine-2S-carboxylate (VI) ranges (2.0-4.0):1; a mass fraction of the concentrated sulfuric acid ranges 90%-98%; the mole ratio between concentrated 98 mass % sulfuric acid and 5-[(benzyloxy) imino] piperidine-2S-carboxylate (VI) ranges (3.0-6.0):1.

According to the present invention, in step (5), the chiral resolution is carried out by using an oxalic acid according to the prior arts.

A method for preparing 5R-[(benzyloxy)amino]piperidine-2S-carboxylate (IIa) further comprises the following step, in addition to steps (1)-(5):

(6) neutralizing the obtained 5R-[(benzyloxy) amino] piperidine-2S-carboxylate oxalate (IIb) in a solvent using a base to obtain 5R-[(benzyloxy) amino] piperidine-2S-carboxylate (IIa).

Preferably, the solvent in step (6) is selected from the group consisting of ethyl acetate, dichloromethane, chloroform, 1,2-dichloroethane, benzene, methylbenzene, and a combination thereof; a mass ratio between the solvent and compound (IIb) ranges from 4:1 to 12:1.

Preferably, the base in step (6) is selected from the group consisting of potassium carbonate, sodium carbonate, calcium carbonate, potassium hydrogencarbonate, sodium hydrogencarbonate, calcium hydrogencarbonate, aqueous ammonia, and a combination thereof; a molar ratio between the base and 5R-[(benzyloxy)amino] piperidine-2S-carboxylate oxalate (IIb) is (1.5-3.0):1.

Preferably, in step (6), the temperature for the neutralizing reaction ranges from 10° C. to 40° C.; preferably, a duration for the neutralization reaction ranges from 2 hours to 5 hours.

It should be noted that in the respective reaction steps, post-treatments to the obtained various intermediates such as separation and washing may be carried out according to the prior arts; the present invention is not limited to the preferred embodiments provided herein.

With 5R-[(benzyloxy) amino] piperidine-2S-carboxylate (IIa) or 5R-[(benzyloxy) amino] piperidine-2S-carboxylate oxalate (IIb) obtained according to the present invention as the starting material, avibactam (I) is prepared according to a known method. The scheme of the method for preparing avibactam (I) is provided below (see scheme 4):

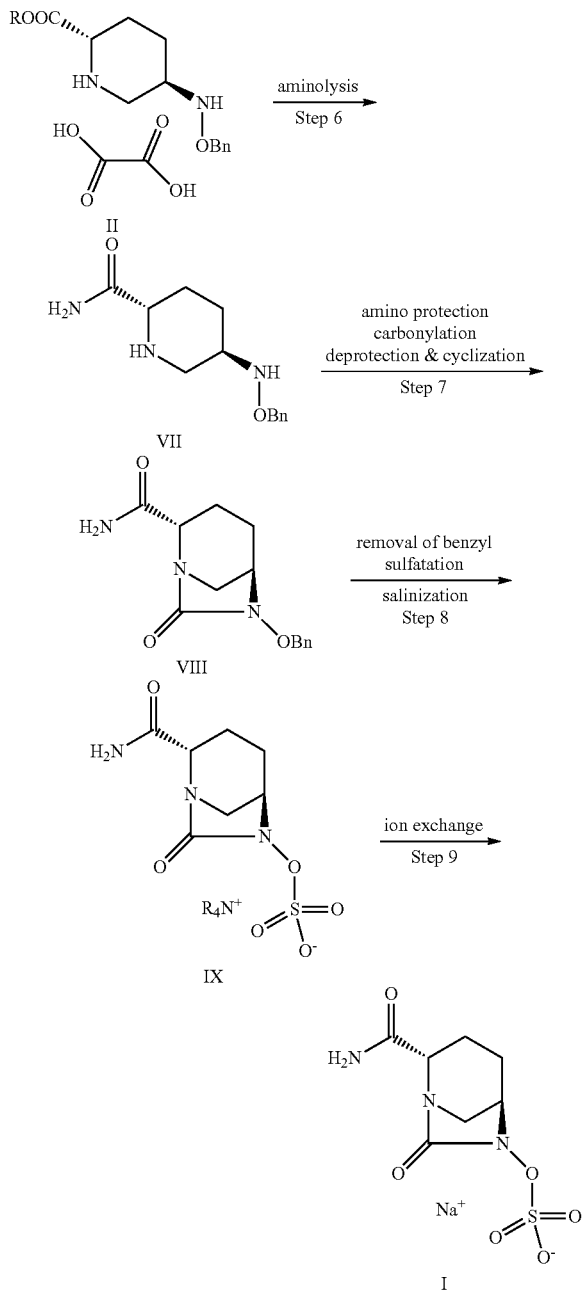

where R denotes H, alkali metal ion or alkaline earth metal ion.

Technical Features and Advantageous Effects of the Present Invention:

1. With L-glutamic acid or the L-glutamic acid sodium salt as the starting material, N-carboxymethyl-L-glutamic acid (III) is obtained through a substitution reaction; the starting material is inexpensive and easily assessible; besides, the molecular structure of the compound is suitable for preparing the target product without a need of a protecting agent as used in the background technologies, and the material has a high atomic economy.

2. The schemes provided by the present invention are novel processes for preparing 5R-[(benzyloxy) amino] piperidine-2S-carboxylate (IIa) and the oxalates thereof; the reactions of respective steps have a high reaction selectivity. For example, based on the controlled reaction temperature and the pH value, in step (1), only the amino is reacted with chloroacetate via an SN2 substitution reaction, and there are no any other groups that may react; therefore, the reaction selectivity reaches up to 100%. The step (2) relates to complete esterification of all of the three carboxyls, wherein the corresponding esterification reaction is only carried out with the carboxyls, such that the reaction selectivity is 100%. In step (3), the intramolecular condensation is carried out, where two manners of cyclization are provided for the six-membered ring. However, after decarboxylation, the same product is obtained from the two manners of cyclization; therefore, the reaction selectivity in this step is 100%. The step (4) relates to the reaction between benzyloxy amine and the carboxyl, wherein under a controlled rate of charge, an imine product may be obtained with a reaction selectivity of near 100%.

3. The inventors have surprisingly found that when using thionyl chloride or triphosgene as the acid reagent to esterify N-carboxymethyl-L-glutamic acid (III), sulfur dioxide or carbon dioxide produced after completion of the reaction can be removed out of the system in the form of gas, which facilitates post-treatment.

4. The starting material for the present invention is inexpensive and easily accessible; the reaction condition is easily controllable; the reaction selectivity is high; the operability is strong; the process is simple; the target product has a high yield, and the like. For example, the total yield of 5R-[(benzyloxy) amino] piperidine-2S-carboxylate oxalate (IIb) is higher than 60% (calculated based on L-glutamic acid monosodium salt, i.e., monosodium glutamate); the highest yield may reach 75%, such that the product has a low cost. Besides, waste liquid discharge is reduced, and the process is green and environment-friendly.

5. As key intermediate compounds, 5R-[(benzyloxy) amino] piperidine-2S-carboxylate (IIa) and 5R-[(benzyloxy) amino] piperidine-2S-carboxylate oxalate (IIb) prepared according to the present disclosure may be used to prepare avibactam (I). The process has a high atomic economy and is green and environment-friendly, thereby facilitating reduction of the cost of avibactam as well as industrial and clean production thereof.

DETAILED DESCRIPTION OF EMBODIMENTS

Figure 1:
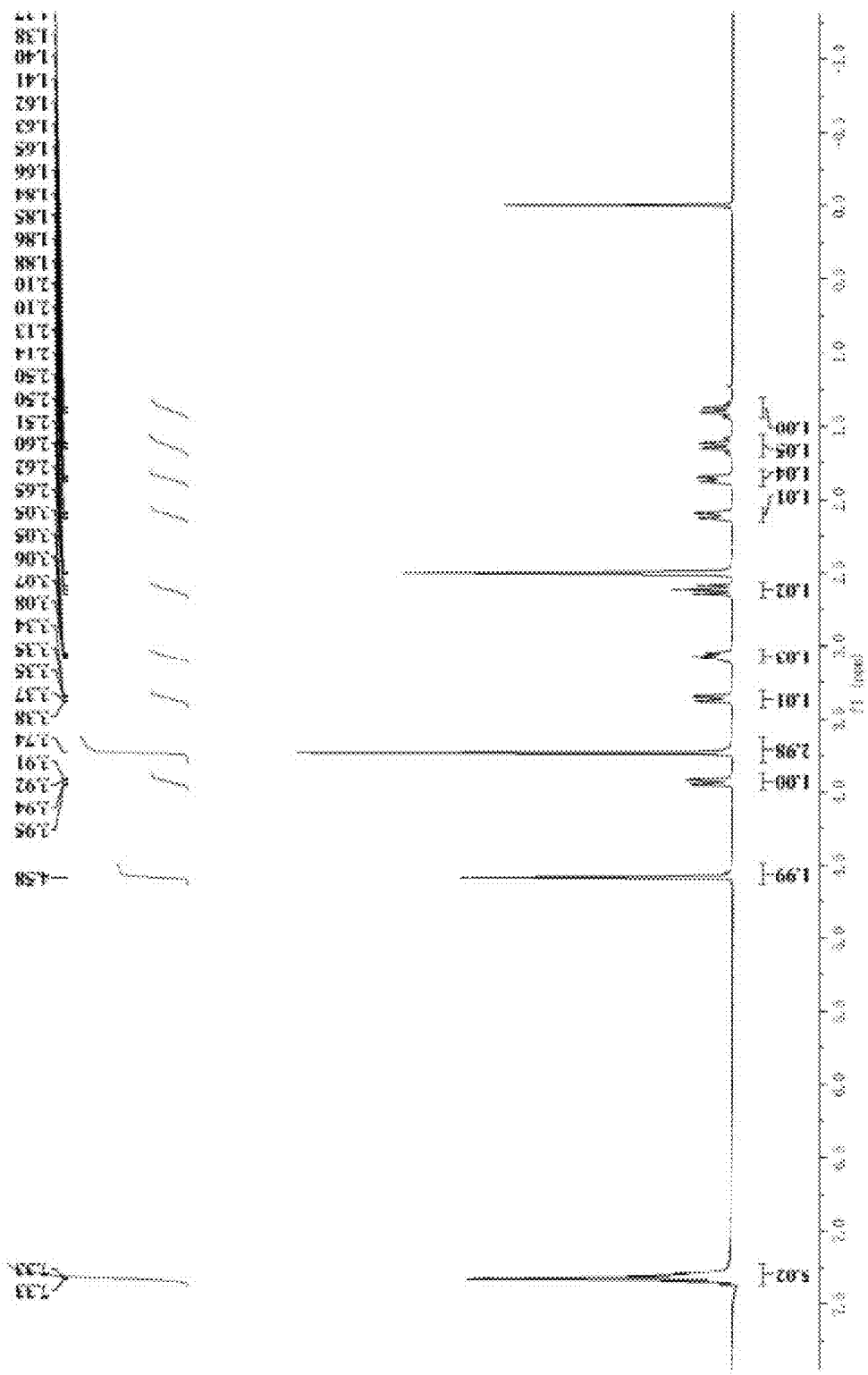
FIG. 1 shows a proton nuclear magnetic resonance spectroscopy of methyl 5R-[(benzyloxy) amino] piperidine-2S-carboxylate oxalate (IIb$_1$)

Hereinafter, the present invention will be illustrated in detail with reference to the examples; however, the present invention is not limited thereto.

The percentages in the examples all refer to mass percentages, unless otherwise indicated.

The reaction process and product purity are monitored by a gas chromatograph or a liquid chromatograph. A liquid chromatograph equipped with a chiral column (ES-OVS, 150 mm×4.6 mm, Agilent) is used to detect the optical purity (area ratio %) and calculate the yield and e.e % value.

Example 1: Preparation of N-carboxymethyl-L-glutamic Acid (III)

To a 500 ml 4-neck flask equipped with a stirrer and a thermometer, 150 g of water and 14.5 g of chloroactic acid were added under stirring. The system pH value was adjusted to 10-11 by adding 30% sodium hydroxide aqueous solution; then, 14.7 g (0.10 mol) of L-glutamic acid was added and stirred to react at 30° C. to 35° C. for 4 hours, and cooled after completion of the reaction. The temperature was kept in a range from 0° C. to 5° C.; then, 30% hydrochloric acid was added dropwise to adjust the system pH value to 2-3. The reaction mixture was filtered, and the obtained filter cake was washed twice by acetone (10 g each), and then dried to obtain 18.5 g of N-carboxymethyl-L-glutamic acid in an HPLC purity of 99.5% and a yield of 90.2%.

Example 2: Preparation of N-carboxymethyl-L-glutamic Acid (III)

To a 500 ml 4-neck flask equipped with a stirrer and a thermometer, 150 g of water and 14.5 g of chloroactic acid were added under stirring. The system pH value was adjusted to 10-11 by adding 20% sodium carbonate aqueous solution; then, 16.9 g (0.10 mol) of L-glutamic acid monosodium salt (monosodium glutamate) was added and stirred to react at 40° C. to 45° C. for 6 hours, and cooled after completion of the reaction. The temperature was kept in a range from 0° C. to 5° C.; then, 30% hydrochloric acid was added dropwise to adjust the system pH value to 2-3. The reaction mixture was filtered, and the obtained filter cake was washed twice by acetone (10 g each), and then dried to obtain 18.9 g of N-carboxymethyl-L-glutamic acid in an HPLC purity of 99.6% and a yield of 92.2%. The obtained N-carboxymethyl-L-glutamic acid (III) was applied to Examples 3, 4 and 5.

Example 3: Preparation of dimethyl N-methoxycarbonylmethyl-L-glutamate ($IV_1$)

To a 1000 ml 4-neck flask equipped with a stirrer, a thermometer, and a reflex condenser (connected to an adsorption device of 30% sodium hydroxide aqueous solution), 350 g of methanol, 20.5 g (0.10 mol) of N-carboxymethyl-L-glutamic acid (III), and 60.0 g (0.5 mol) of thionyl chloride were added. The reaction mixture was heated to react at 60° C. to 65° C. for 7 hours. After cooling to 20° C. to 25° C., hydrogen chloride gas in the system was replaced with nitrogen. After replacing for 30 minutes, distilling was carried out to recover excess thionyl chloride and methanol; then 350 g of fresh methanol, 34.5 g (0.25 mol) of potassium carbonate were added to the residual and stirred at 20° C. to 25° C. for 1 hour. The reaction mixture was filtered, and the obtained filter cake was washed twice by methanol (50 g each). The filtrates were combined and distilled at a normal pressure to recover methanol, and then distilled at a reduced pressure to obtain 22.1 g of dimethyl N-methoxycarbonylmethyl-L-glutamate as colorless transparent liquid, in an HPLC purity of 99.5% and a yield of 89.5%. The obtained dimethyl N-carbomethoxymethyl-L-glutamate ($IV_1$) was applied to Example 6.

Example 4: Preparation of diethyl N-ethoxycarbonylmethyl-L-glutamate ($IV_2$)

To a 1000 ml 4-neck flask equipped with a stirrer, a thermometer, and a reflex condenser (connected to an adsorption device of 30% sodium hydroxide aqueous solution), 400 g of ethanol, 20.5 g (0.10 mol) of N-carboxymethyl-L-glutamic acid (III), and 19.5 g (0.2 mol) of triphosgene were added. The reaction mixture was heated to react at 70° C. to 75° C. for 6 hours. After cooling to 20° C.-25° C., hydrogen chloride gas in the system was replaced with nitrogen. After replacing for 30 minutes, distilling was carried out to recover ethanol; then 400 g of fresh ethanol, 34.5 g (0.25 mol) of potassium carbonate were added to the residual and stirred at 20° C. to 25° C. for 1 hour. The reaction mixture was filtered, and the obtained filter cake was washed twice by ethanol (50 g each). The filtrates were combined and distilled at a normal pressure to recover ethanol, and then distilled at a reduced pressure to obtain 26.7 g of diethyl N-ethoxycarbonylmethyl-L-glutamate as colorless transparent liquid in an HPLC purity of 99.7% and a yield of 92.3%. The obtained diethyl N-ethoxycarbonylmethyl-L-glutamate ($IV_2$) was applied to Example 7.

Example 5: Preparation of dibenzyl N-benzyloxycarbonylmethyl-L-glutamate ($IV_3$)

To a 1000 ml 4-neck flask equipped with a stirrer, a thermometer, and a reflex condenser (connected to an adsorption device of 30% sodium hydroxide aqueous solution), 300 g of benzyl alcohol, 20.5 g (0.10 mol) of N-carboxymethyl-L-glutamic acid (III), and 60.0 g (0.5 mol) of thionyl chloride were added, and then reacted at 80° C. to 85° C. for 6 hours. After cooling to 20° C.-25° C., hydrogen chloride gas in the system was replaced with nitrogen. After replacing for 1 hour, distilling was carried out to recover excess thionyl chloride and benzyl alcohol; then 400 g of fresh benzyl alcohol and 34.5 g (0.25 mol) of potassium carbonate added to the residual and stirred at 20° C. to 25° C. for 1 hour. The reaction mixture was filtered, and the obtained filter cake was washed twice by benzyl alcohol (100 g each). The filtrates were combined and distilled at a normal pressure to recover benzyl alcohol, and then distilled at a reduced pressure to obtain 43.5 g of dibenzyl N-benzyloxycarbonylmethyl-L-glutamate as yellowish transparent liquid in an HPLC purity of 99.1% and a yield of 91.6%. The obtained dibenzyl N-benzyloxycarbonylmethyl-L-glutamate ($IV_3$) was applied to Example 8.

Example 6: Preparation of methyl piperidine-5-one-2S-carboxylate ($V_1$)

To a 500 ml 4-neck flask equipped with a stirrer and a thermometer, 200 g of tetrahydrofuran, 6.0 g (0.11 mol) of sodium methoxide were added and cooled to −5° C. to 0° C., and at such temperature a solution of 24.5 g (0.1 mol) of dimethyl N-methoxycarbonylmethyl-L-glutamate ($IV_1$) in tetrahydrofuran (20 g) was added dropwise, then stirred for reaction at 20° C. to 25° C. for 4 hours. The reaction mixture was filtered, and the filter cake was washed twice by tetrahydrofuran (50 g each), and then the filtrates were combined and distilled at a normal pressure to recover tetrahydrofuran. 100 g of water, 15 g of 30% hydrochloric acid, and 200 g of 1,2-dichloroethane were added to the obtained solid, and then stirred at 20° C. to 25° C. for hydrolysis reaction for 2 hours. Then, the solution was separated and an aqueous phase was extracted by 1,2-dichloroethane (50 g each); the organic phases were combined and added with 200 g of methanol and 30.0 g (0.25 mol) of thionyl chloride, then heated for esterification reaction at 60° C. to 65° C. for 7 hours.

The product was then subjected to post-treatments. After cooling to 20° C.-25° C., hydrogen chloride gas in the system was replaced with nitrogen. And after replacing for 30 minutes, distilling was carried out to recover excess thionyl chloride, methanol, and 1,2-dichloroethane; then 350 g of fresh methanol and 34.5 g (0.25 mol) of potassium carbonate were added to the residual and stirred at 20° C. to 25° C. for 1 hour, and then the mixture was filtered; and the obtained filter cake was washed twice by methanol (50 g each); the filtrates were combined and distilled at a normal pressure to recover methanol, and then distilled at a reduced pressure to obtain 13.7 g of methyl piperidine-5-one-2S-carboxylate ($V_1$) as colorless transparent liquid in a GC purity of 99.6% and a yield of 87.5%. The obtained methyl piperidine-5-one-2S-carboxylate ($V_1$) was applied to Example 9.

Example 7: Preparation of ethyl piperidine-5-one-2S-carboxylate ($V_2$)

To a 500 ml 4-neck flask equipped with a stirrer and a thermometer, 200 g of tetrahydrofuran, 7.5 g (0.11 mol) of sodium ethoxide were added and cooled to −5° C. to 0° C., and at such temperature a solution of 29.0 g (0.1 mol) of diethyl N-ethoxycarbonylmethyl-L-glutamate ($IV_2$) in tetrahydrofuran (20 g) was added dropwise, then stirred for reaction at 20° C. to 25° C. for 4 hours. The reaction mixture was filtered, and the filter cake was washed twice by tetrahydrofuran (50 g each); and then the filtrates were combined and distilled at a normal pressure to recover tetrahydrofuran. 100 g of water, 15 g of 30% hydrochloric acid, and 200 g of 1,2-dichloroethane were added to the obtained solid, and then stirred at 20° C. to 25° C. for reaction for 2 hours. Then, the solution was separated and an aqueous phase was extracted by 1,2-dichloroethane (50 g each); the organic phases were combined and added with 300 g of ethanol and 30.0 g (0.1 mol) of triphosgene, then heated for reaction at 60° C. to 65° C. for 7 hours. After cooling to 20° C.-25° C., hydrogen chloride gas in the system was replaced with nitrogen. After replacing for 50 minutes, distilling was carried out to recover 1,2-dichloroethane and ethanol; then 350 g of fresh ethanol and 34.5 g (0.25 mol) of potassium carbonate were added to the residual and stirred at 20° C. to 25° C. for 1 hour. The reaction mixture was filtered, and the obtained filter cake was washed twice by ethanol (50 g each); the filtrates were combined, and the organic phases were combined and distilled at a normal pressure to recover ethanol, and then distilled at a reduced pressure to obtain 15.2 g of ethyl piperidine-5-one-2S-carboxylate ($V_2$) as colorless transparent liquid in a GC purity of 99.8% and a yield of 89.2%. The obtained ethyl piperidine-5-one-2S-carboxylate ($V_2$) was applied to Example 10.

Example 8: Preparation of Benzyl piperidine-5-one-2S-carboxylate ($V_3$)

To a 500 ml 4-neck flask equipped with a stirrer and a thermometer, 250 g of tetrahydrofuran, 4.1 g (0.1 mol) of 60% sodium hydride were added and cooled to −5° C. to 0° C., and at such temperature a solution of 47.5 g (0.1 mol) of dibenzyl N-benzylcarbonylmethyl-L-glutamate ($IV_3$) in tetrahydrofuran (20 g) was added dropwise, then stirred for reaction at 20° C. to 25° C. for 5 hours. The reaction mixture was filtered, and the filter cake was washed twice by tetrahydrofuran (50 g each); and then the filtrates were combined and distilled at a normal pressure to recover tetrahydrofuran. 100 g of water, 15 g of 30% hydrochloric acid, and 200 g of 1,2-dichloroethane were added to the obtained solid, and then stirred at 20° C. to 25° C. for reaction for 3 hours. Then, the solution was separated and an aqueous phase was extracted by 1,2-dichloroethane (100 g each); the organic phases were combined and added with 250 g of benzyl alcohol and 30.0 g (0.25 mol) of thionyl chloride, then heated for reaction at 80° C. to 85° C. for 7 hours. After cooling to 20° C.-25° C., hydrogen chloride gas in the system was replaced with nitrogen. After replacing for 50 minutes, distilling was carried out to recover excess thionyl chloride, 1,2-dichloroethane, and benzyl alcohol; then 350 g of fresh benzyl alcohol and 34.5 g (0.25 mol) of potassium carbonate were added to the residual and stirred at 20° C. to 25° C. for 1 hour. The filtrates were filtered, and the obtained filter cake was washed twice by benzyl alcohol (100 g each); the filtrates were combined and distilled at a reduced pressure to recover benzyl alcohol, and then further distilled at a reduced pressure to obtain 20.6 g of benzyl piperidine-5-one-2S-carboxylate ($V_3$) as yellowish transparent liquid in a GC purity of 99.5% and a yield of 88.6%. The obtained benzyl piperidine-5-one-2S-carboxylate ($V_3$) was applied to Example 11.

Example 9: Preparation of methyl 5-[(benzyloxy)imino] piperidine-2S-carboxylate ($VI_1$)

To a 500 ml 4-neck flask equipped with a stirrer, a thermometer, and a reflex condenser, 220 g of ethyl acetate, 20.5 g (0.16 mol) of methyl piperidine-5-one-2S-carboxylate ($V_1$), 27.0 g (0.17 mol) of benzyloxyamine hydrochloride, and 18.2 g (0.18 mol) of triethylamine were added and stirred for reaction at 50° C. to 55° C. for 4 hours. After cooling, 100 g of water was added; the solution was separated and then an organic phase was washed twice by saturated saline (25 g each). The organic phase was distilled to recover the solvent and then distilled at a reduced pressure to obtain methyl 5-[(benzyloxy)imino]piperidine-2S-carboxylate as yellowish transparent liquid in a GC purity of 98.0% and a yield of 98.5%. The obtained methyl 5-[(benzyloxy)imino]piperidine-2S-carboxylate ($VI_1$) was applied to Example 12.

Example 10: Preparation of ethyl 5-[(benzyloxy)imino] piperidine-2S-carboxylate ($VI_2$)

To a 500 ml 4-neck flask equipped with a stirrer, a thermometer, and a reflex condenser, 250 g of 1,2-dichloroethane, 26.0 g (0.15 mol) of ethyl piperidine-5-one-2S-carboxylate ($V_2$), 26.0 g (0.16 mol) of benzyloxyamine hydrochloride, and 17.2 g (0.17 mol) of triethylamine were added and stirred for reaction at 50° C. to 55° C. for 4 hours. After cooling, 100 g of water was added; the solution was separated and then an organic phase was washed twice by saturated saline (25 g each). The organic phase was distilled to recover the solvent and then distilled at a reduced pressure to obtain ethyl 5-[(benzyloxy)imino]piperidine-2S-carboxylate as yellowish transparent liquid in a GC purity of 98.2% and a yield of 98.5%. The obtained ethyl 5-[(benzyloxy)imino]piperidine-2S-carboxylate (VI$_3$) was applied to Example 13.

Example 11: Preparation of Benzyl 5-[(benzyloxy)imino] piperidine-2S-carboxylate (VI$_3$)

To a 500 ml 4-neck flask equipped with a stirrer, a thermometer, and a reflex condenser, 250 g of ethyl acetate, 37.0 g (0.16 mol) of benzyl piperidine-5-one-2S-carboxylate (V$_3$), 27.0 g (0.17 mol) of benzyloxyamine hydrochloride, and 18.2 g (0.18 mol) of triethylamine were added and stirred for reaction at 60° C. to 65° C. for 4 hours. After cooling, 100 g of water was added; the solution was separated and then an organic phase was washed twice by saturated saline (25 g each). The organic phase was distilled to recover the solvent and then distilled at a reduced pressure to obtain benzyl 5-[(benzyloxy)imino]piperidine-2S-carboxylate as yellowish transparent liquid in a GC purity of 98.0% and a yield of 99.5%. The obtained benzyl 5-[(benzyloxy)imino]piperidine-2S-carboxylate (VI$_3$) was applied to Example 14.

Example 12: Preparation of methyl 5R-[(benzyloxy)amino] piperidine-2S-carboxylate Oxalate (IIb$_1$)

To a 500 ml 4-neck flask equipped with a stirrer and a thermometer, 200 g of ethyl acetate and 21.0 g (0.08 mol) of methyl 5-[(benzyloxy)imino]piperidine-2S-carboxylate (VI$_1$) were added, then 40.3 g (0.4 mol) of concentrated sulfuric acid was added dropwise at −20° C., and then stirred for 1 hour.

38.0 g (0.18 mol) of sodium triacetoxyborohydride was added at −20° C., then stirred to react at −20° C. to −15° C. for 5 hours. The mixture was kept at a temperature below 10° C., and then added with 100 g of water to quench the reaction, and neutralized with aqueous ammonia. The solution was then separated and an organic phase was washed twice by saturated saline (25 g each). The organic phase was concentrated to recover the solvent, then 80 g of ethyl acetate, 40 g of methanol, and 10.4 g (0.08 mol) of oxalic acid dihydrate were added to the residual and heated to 45° C., stirred for 1 hour, and then cooled and filtered. The obtained filter cake was first washed with a mixed liquid of 60 g of ethyl acetate/methanol (2:1) and then washed with 50 g of ethyl acetate. After drying under vacuum, methyl 5R-[(benzyloxy)amino]piperidine-2S-carboxylate oxalate (IIb$_1$) as a single isomer was obtained in a chiral HPLC purity of 99.5%. The total yield was 63.5% (calculated based on the added L-glutamic acid monosodium salt (i.e., monosodium glutamate)).

The spectroscopy of the product is shown in FIG. 1 and the NMR data are provided below:
$^1$HNMR (400 MHz, DMSO-d6) δ: 1.40 (1H, q), 1.64 (1H, q), 1.85 (1H, d), 2.12 (1H, dd), 2.62 (1H, t), 3.06 (1H, m), 3.36 (1H, d), 3.74 (3H, s), 3.93 (1H, dd), 4.58 (2H, s), 7.33 (5H, m).

Example 13: Preparing of ethyl 5R-[(benzyloxy)amino] piperidine-2S-carboxylate Oxalate (IIb$_2$)

To a 500 ml 4-neck flask equipped with a stirrer and a thermometer, 200 g of ethyl acetate and 22.0 g (0.08 mol) of ethyl 5-[(benzyloxy)imino]piperidine-2S-carboxylate (VI$_2$) were added, then 40.3 g (0.4 mol) of concentrated sulfuric acid added dropwise at −20° C., and then stirred for 1 hour. At −20° C., 38.0 g (0.18 mol) of sodium triacetoxyborohydride was added, then stirred to react at −20° C. to −15° C. for 5 hours. The mixture was kept at a temperature below 10° C., and then added with 100 g of water to quench the reaction, and neutralized with aqueous ammonia. The solution was then separated and an organic phase was washed twice by saturated saline (25 g each). The organic phase was concentrated to recover the solvent, then 80 g of ethyl acetate, 40 g of methanol, and 10.4 g (0.08 mol) of oxalic acid dihydrate were added to the residual and heated to 45° C., stirred for 1 hour, and then cooled and filtered. The obtained filter cake was first washed with a mixed liquid of 60 g of ethyl acetate/methanol (2:1) and then washed with 50 g of ethyl acetate. After drying under vacuum, ethyl 5R-[(benzyloxy)amino]piperidine-2S-carboxylate oxalate (IIb$_2$) as a single isomer was obtained in a chiral HPLC purity of 99.6%. The total yield was 65.4% (calculated based on the added L-glutamic acid monosodium salt (i.e., monosodium glutamate)).

Figure 2:
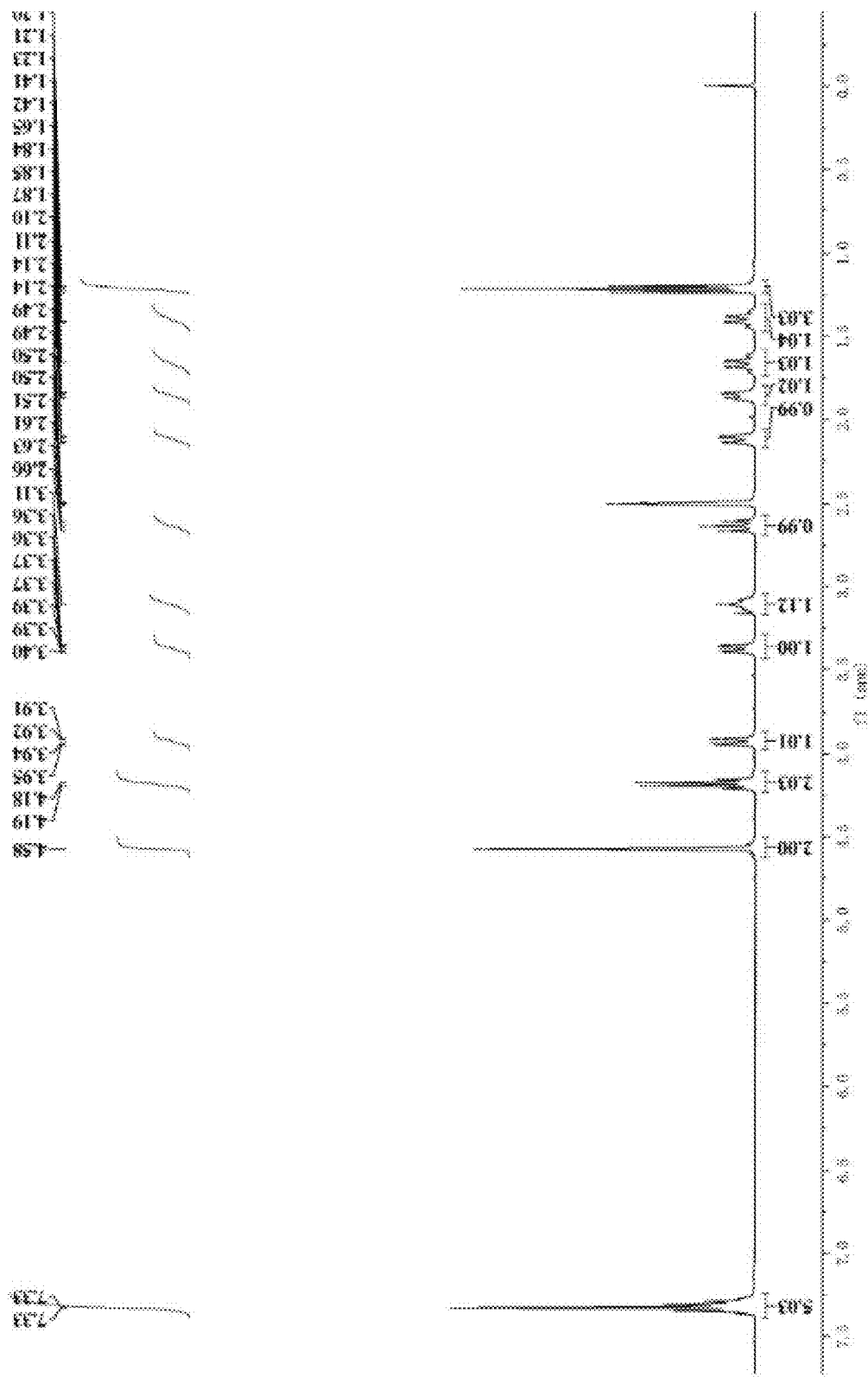
FIG. 2 shows a proton nuclear magnetic resonance spectroscopy of ethyl 5R-[(benzyloxy) amino] piperidine-2S-carboxylate oxalate (IIb$_2$)

The spectroscopy of the product is shown in FIG. 2 and the NMR data are provided below:
$^1$HNMR (400 MHz, DMSO-d6) δ: 1.21 (3H, t), 1.41 (1H, q), 1.68 (1H, q), 1.85 (1H, d), 2.13 (1H, dd), 2.62 (1H, t), 3.11 (1H, m), 3.38 (1H, d), 3.93 (1H, dd), 4.18 (2H, q), 4.58 (2H, s), 7.33 (5H, m).

Example 14: Preparation of benzyl 5R-[(benzyloxy)amino] piperidine-2S-carboxylate Oxalate (IIb$_3$)

To a 500 ml 4-neck flask equipped with a stirrer and a thermometer, 200 g of ethyl acetate and 27.0 g (0.08 mol) of benzyl 5-[(benzyloxy)imino]piperidine-2S-carboxylate (VI$_3$) were added, then 40.3 g (0.4 mol) of concentrated sulfuric acid was added dropwise at −20° C. and stirred for 1 hour. At −20° C., 38.0 g (0.18 mol) of sodium triacetoxyborohydride was added, then stirred to react at −20° C. to −15° C. for 5 hours. The mixture was kept at a temperature below 10° C., and then added with 100 g of water to quench the reaction, and neutralized with aqueous ammonia. The solution was then separated and an organic phase was washed twice by saturated saline (25 g each). The organic phase was concentrated to recover the solvent, then 80 g of ethyl acetate, 40 g of methanol, and 10.4 g (0.08 mol) of oxalic acid dihydrate were added to the residual and heated to 45° C., stirred for 1 hour, and then cooled and filtered. The obtained filter cake was first washed with a mixed liquid of 60 g of ethyl acetate/methanol (2:1) and then washed with 50 g of ethyl acetate. After drying under vacuum, benzyl 5R-[(benzyloxy)amino]piperidine-2S-carboxylate oxalate (IIb$_3$) as a single isomer was obtained in a chiral HPLC purity of 99.5%. The total yield was 65.0% (calculated based on the added L-glutamic acid monosodium salt (i.e., monosodium glutamate)).

Figure 3:
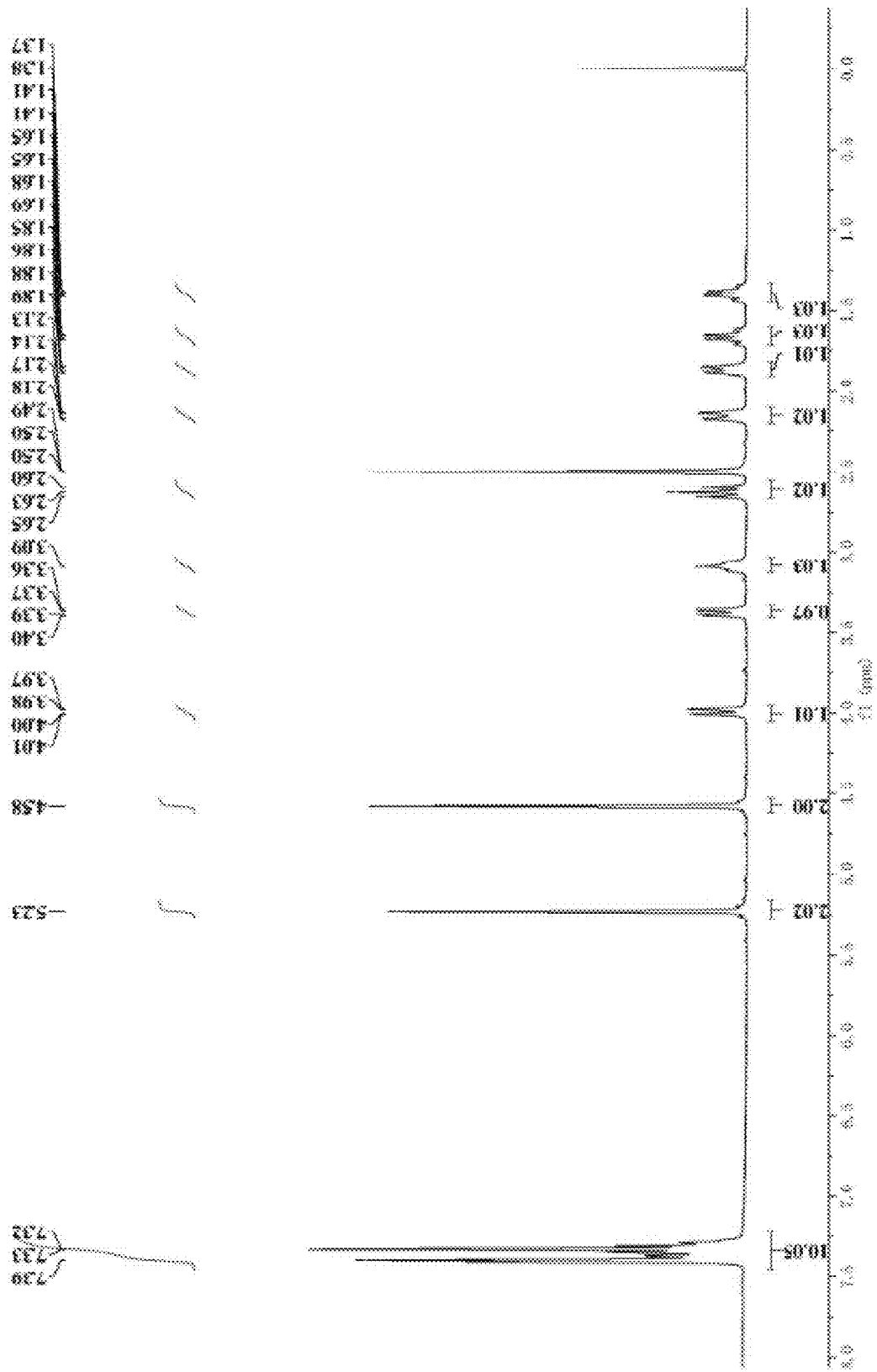
FIG. 3 shows a proton nuclear magnetic resonance spectroscopy of benzyl 5R-[(benzyloxy) amino] piperidine-2S-carboxylate oxalate (IIb$_3$).

The spectroscopy of the product is shown in FIG. 3 and the NMR data are provided below:
$^1$HNMR (400 MHz, DMSO-d6) δ: 1.41 (1H, q), 1.68 (1H, q), 1.88 (1H, d), 2.17 (1H, dd), 2.62 (1H, t), 3.09 (1H, m), 3.38 (1H, d), 3.99 (1H, dd), 4.58 (2H, s), 5.23 (2H, s), 7.35 (10H, m).

Example 15: Preparation of methyl 5R-[(benzyloxy)amino] piperidine-2S-carboxylate (IIa$_1$)

To a 500 ml 4-neck flask equipped with a stirrer and a thermometer, 300 g of ethyl acetate, 42.5 g (0.12 mol) of methyl 5R-[(benzyloxy)amino]piperidine-2S-carboxylate oxalate (IIb₁), and 100 g (0.24 mol) of 20% sodium bicarbonate solution were added and stirred at 30° C. to 35° C. for 2 hours. The solution was separated and then an aqueous phase was extracted twice by ethyl acetate (60 g each). The organic phases were combined and washed twice by the saturated sodium chloride solution (50 g each). The organic phase distilled to recover the solvent and then distilled at a reduced pressure to obtain methyl 5R-[(benzyloxy)amino] piperidine-2S-carboxylate as yellowish viscous oil in a GC purity of 99.8% and a yield of 97.3%.

Example 16: Preparation of ethyl 5R-[(benzyloxy) amino]piperidine-2S-carboxylate (IIa₂)

To a 500 ml 4-neck flask equipped with a stirrer and a thermometer, 300 g of ethyl acetate, 44.0 g (0.12 mol) of ethyl 5R-[(benzyloxy)amino]piperidine-2S-carboxylate oxalate (IIb₂), and 100 g (0.24 mol) of 20% sodium bicarbonate solution were added and stirred at 20° C. to 25° C. for 2 hours. The solution was separated and then an aqueous phase was extracted twice by ethyl acetate (60 g each). The organic phases were combined and washed twice by the saturated sodium chloride solution (50 g each). The organic phase was distilled to recover the solvent and then distilled at a reduced pressure to obtain ethyl 5R-[(benzyloxy)amino] piperidine-2S-carboxylate as yellowish viscous oil in a GC purity of 99.5% and a yield of 96.8%.

Example 17: Preparation of benzyl 5R-[(benzyloxy) amino] piperidine-2S-carboxylate (IIa₃)

To a 500 ml 4-neck flask equipped with a stirrer and a thermometer, 350 g of ethyl acetate, 51.0 g (0.12 mol) of benzyl 5R-[(benzyloxy) amino] piperidine-2S-carboxylate oxalate (IIb₃), and 100 g (0.24 mol) of 20% sodium bicarbonate solution were added and stirred at 30° C. to 35° C. for 3 hours. The solution was separated and then an aqueous phase was extracted twice by ethyl acetate (100 g each). The organic phases were combined and washed twice by the saturated sodium chloride solution (50 g each). The organic phase was distilled to recover the solvent and then distilled at a reduced pressure to obtain benzyl 5R-[(benzyloxy) amino]piperidine-2S-carboxylate as yellowish viscous oil in a GC purity of 99.6% and a yield of 96.5%.

What is claimed is:

1. A process for preparing 5R-[(benzyloxy) amino] piperidine-2S-carboxylate oxalate, comprising:
   (1) subjecting L-glutamic acid or L-glutamic acid sodium salt to a substitution reaction with chloroactic acid at 10° C. to 70° C. under an alkaline condition provided by an inorganic base or an organic base to obtain N-carboxymethyl-L-glutamic acid (III);
   (2) subjecting N-carboxymethyl-L-glutamic acid (III) and alcohol to an esterification reaction in the presence of an acid reagent to prepare N-alkoxycarbonyl methyl-L-glutamic acid diester (IV); wherein the acid reagent is thionyl chloride or triphosgene;
   (3) subjecting N-alkoxycarbonyl methyl-L-glutamic acid diester (IV) to an intramolecular condensation reaction under the action of a solvent and a strong base; and subjecting the condensed product to a hydrolysis-decarboxylation reaction and an esterification reaction to obtain piperidine-5-one-2S-carboxylate (V); wherein the solvent is tetrahydrofuran, 2-methyltetrahydrofuran or methoxycyclopentane; the hydrolysis-decarboxylation reaction is carried out under the action of an inorganic acid; the esterification reaction is carried out in the presence of thionyl chloride or triphosgene and alcohol;
   (4) condensing the obtained piperidine-5-one-2S-carboxylate (V) and benzyloxylamine hydrochloride in a solvent in the presence of the organic base to obtain 5-[(benzyloxy)imino] piperidine-2S-carboxylate (VI);
   (5) subjecting 5-[(benzyloxy)imino] piperidine-2S-carboxylate (VI) to a selective reduction and a chiral resolution to obtain 5R-[(benzyloxy) amino] piperidine-2S-carboxylate oxalate (IIb).

2. The process for preparing 5R-[(benzyloxy) amino] piperidine-2S-carboxylate oxalate according to claim 1, wherein in step (1), the inorganic base is selected from the group consisting of sodium hydroxide, potassium hydroxide, potassium carbonate, sodium carbonate, calcium carbonate, potassium hydrogencarbonate, sodium hydrogencarbonate, calcium hydrogencarbonate, potassium acetate, sodium acetate, calcium acetate and a combination thereof; and the organic base is selected from the group consisting of trimethylamine, triethylamine, tri-n-butylamine, and a combination thereof; preferably, the L-glutamic acid sodium salt is one of L-glutamic acid monosodium salt and L-glutamic acid disodium salt.

3. The process for preparing 5R-[(benzyloxy) amino] piperidine-2S-carboxylate oxalate according to claim 1, wherein in step (1), a mole ratio of chloroactic acid:the inorganic base or the organic base: L-glutamic acid or L-glutamic acid sodium salt is (1.0-3.0):(1.0-4.0):1; preferably, the reaction temperature in step (1) ranges from 25° C. to 55° C.

4. The process for preparing 5R-[(benzyloxy) amino] piperidine-2S-carboxylate oxalate according to claim 1, wherein in step (2), when the acid reagent is thionyl chloride, a molar ratio between thionyl chloride and N-carboxymethyl-L-glutamic acid (III) is (3.0-6.0):1; the temperature for the esterification reaction ranges from 30° C. to 95° C.; preferably, in step (2), when the acid reagent is triphosgene, a mole ratio between triphosgene and N-carboxymethyl-L-glutamic acid (III) is (1.0-2.0):1; and the temperature for the esterification reaction ranges from 50° C. to 100° C.

5. The process for preparing 5R-[(benzyloxy) amino] piperidine-2S-carboxylate oxalate according to claim 1, wherein in step (2), the alcohol is selected from the group consisting of methanol, ethanol, n-propanol, isopropanol, n-butanol, isobutanol, tert-butanol, n-pentanol, isopentanol, tert-pentanol, and hexanol; or the alcohol is selected from one of benzyl alcohol, o-methyl benzyl alcohol, and p-methyl benzyl alcohol; preferably, a mass ratio between the alcohol and N-carboxymethyl-L-glutamic acid (III) is (1-30):1.

6. The process for preparing 5R-[(benzyloxy) amino] piperidine-2S-carboxylate oxalate according to claim 1, wherein in step (3), a mass ratio between the solvent and N-alkoxycarbonyl methyl-L-glutamic acid diester (IV) ranges from 4:1 to 20:1; the strong base is selected from the group consisting of sodium hydride, sodium methoxide, sodium ethoxide, sodium t-butoxide, potassium t-butoxide and sodium benzyloxide; preferably, a molar ratio between the strong base and N-alkoxycarbonyl methyl-L-glutamic acid diester (IV) is (1.0-2.0):1.

7. The process for preparing 5R-[(benzyloxy) amino] piperidine-2S-carboxylate oxalate according to claim 1, wherein in step (3), the temperature for the hydrolysis-ecarboxylation reaction ranges from 20° C. to 60° C., preferably the alcohol used for the esterification reaction is methanol, ethanol or benzyl alcohol, and a mass ratio between the alcohol and N-alkoxycarbonyl methyl-L-glutamic acid diester (IV) is (1-30):1; a molar ratio between thionyl chloride or triphosgene and N-alkoxycarbonyl methyl-L-glutamic acid diester (IV) is (0.3-3.0): 1, and the temperature for the esterification reaction ranges from 50° C. to 100° C.

8. The process for preparing 5R-[(benzyloxy) amino] piperidine-2S-carboxylate oxalate according to claim 1, wherein in step (4), the solvent is selected from the group consisting of ethyl acetate, dichloromethane, chloroform, 1,2-dichloroethane, benzene, methylbenzene and a combination thereof; the organic base is selected from the group consisting of trimethylamine, triethylamine, and tri-n-butylamine and a combination thereof; preferably, a mass ratio between the solvent and piperidine-5-one-2S-carboxylate (V) ranges from 4:1 to 12:1; a molar ratio between benzyloxyamine hydrochloride and piperidine-5-one-2S-carboxylate (V) is (0.9-1.5):1; and the temperature ranges from 40° C. to 80° C.

9. The process for preparing 5R-[(benzyloxy) amino] piperidine-2S-carboxylate oxalate according to claim 1, wherein in step (5), the selective reduction is carried out by adding a reducing agent added in ethyl acetate in the presence of concentrated sulfuric acid; preferably, the reducing agent is selected from the group consisting of sodium borohydride, sodium tricyanoborohydride, sodium triacetoxyborohydride, sodium tripropionyloxyborohydride, potassium borohydride, potassium tricyanoborohydride, potassium triacetoxyborohydride or potassium triproloxyborohydride; preferably, a molar ratio between the reducing agent and 5-phenylmethoxyiminopropane piperidine-2S-carboxylate (VI) ranges (2.0-4.0):1.

10. A method for preparing 5R-[(benzyloxy) amino] piperidine-2S-carboxylate (IIa), comprising the steps of preparing 5R-[(benzyloxy) amino] piperidine-2S-carboxylate oxalate according to any one of claims 1-9, and a step of neutralizing the obtained 5R-[(benzyloxy) amino] piperidine-2S-carboxylate oxalate (IIb) in a solvent by a base to obtain 5R-[(benzyloxy) amino] piperidine-2S-carboxylate (IIa), wherein:

the solvent is selected from the group consisting of ethyl acetate, dichloromethane, chloroform, 1,2-dichloroethane, benzene, and methylbenzene, or a combination thereof; a mass ratio between the solvent and compound (IIb) ranges from 4:1 to 12:1; preferably, a molar ratio between the base and 5R-[(benzyloxy) amino] piperidine-2S-carboxylate oxalate (IIb) is (1.5-3.0):1.

\* \* \* \* \*